US006616771B2

United States Patent
Osborne et al.

(10) Patent No.: US 6,616,771 B2
(45) Date of Patent: Sep. 9, 2003

(54) METHOD AND SYSTEM FOR CLEANING AND REUSING A CANNULA

(75) Inventors: Joel A. Osborne, Oklahoma City, OK (US); Dennis Tribble, Oklahoma City, OK (US); William C. Aven, Edmond, OK (US)

(73) Assignee: Forhealth Technologies, Inc., Oklahoma, OK (US)

( * ) Notice: Subject to any disclaimer, the term of this patent is extended or adjusted under 35 U.S.C. 154(b) by 0 days.

(21) Appl. No.: 09/999,188

(22) Filed: Nov. 30, 2001

(65) Prior Publication Data

US 2003/0102012 A1 Jun. 5, 2003

(51) Int. Cl.[7] .............................. B08B 3/00; B08B 3/12; B08B 9/00; B08B 9/023; B08B 9/027
(52) U.S. Cl. .................. 134/18; 134/22.1; 134/22.11; 134/22.12; 134/22.18; 134/22.14; 134/22.19; 134/23; 134/24; 134/26; 134/57 R; 134/61; 134/66; 134/80; 134/170; 134/186
(58) Field of Search ........................... 134/1, 18, 22.1, 134/22.11, 22.12, 22.18, 23, 22.14, 24, 22.19, 26, 57 R, 61, 66, 80, 170, 186

(56) References Cited

U.S. PATENT DOCUMENTS

| | | | | |
|---|---|---|---|---|
| 5,755,894 A | * | 5/1998 | Bowman et al. | ......... 134/22.12 |
| 5,805,454 A | | 9/1998 | Valerino, Sr. et al. | |
| 5,985,038 A | * | 11/1999 | Dawson | ........................ 134/1 |
| 6,048,086 A | | 4/2000 | Valerino, Sr. | |

* cited by examiner

Primary Examiner—Zeinab El-Arini
(74) Attorney, Agent, or Firm—Darby & Darby (57) ABSTRACT

A computer-implemented method and system for cleaning a contaminated cannula so that it may be reused includes moving the contaminated cannula from a drug reconstitution station where the cannula is used to prepare a drug solution into a first rinsing station where the cannula is cleaned. A database is referred to to determine what drug solution the cannula has been contaminated with, and to determine a first amount of cleaning fluid that needs to be passed internally through the cannula, and a second amount of cleaning fluid that needs to be passed externally about the cannula so that there is effectively no contaminant remaining inside and outside of the cannula. The first amount of cleaning fluid is passed internally through the cannula. The second amount of cleaning fluid is passed externally about the cannula. After the cannula is cleaned, the cannula is moved to the drug reconstitution station to prepare another drug solution.

28 Claims, 7 Drawing Sheets

METHOD AND SYSTEM FOR CLEANING AND REUSING A CANNULA

BACKGROUND OF THE INVENTION

1. Field of the Invention

The present invention relates generally to medical equipment, and more particularly, to an automated apparatus for cleaning a cannula so that it may be reused to reconstitute one or more medications that are prepared in a vial and stored in a syringe.

2. Discussion of the Related Art

Disposable syringes are in widespread use for a number of different types of applications. For example, syringes are used not only to withdraw a fluid (e.g., blood) from a patient, but also to administer a medication to a patient. In the latter, a cap or the like is removed from the syringe and a unit dose of the medication is carefully measured and then injected or otherwise disposed within the syringe.

As technology advances, more and more sophisticated, automated systems are being developed for preparing and delivering medications by integrating a number of different stations, with one or more specific tasks being performed at each station. For example, one type of exemplary automated system operates as a syringe filling apparatus that receives user inputted information, such as the type of medication, the volume of the medication and any mixing instructions, etc. The system then uses this inputted information to disperse the correct medication into the syringe up to the inputted volume.

In some instances, the medication that is to be delivered to the patient includes more than one pharmaceutical substance. For example, the medication can be a mixture of several components, such as several pharmaceutical substances.

By automating the medication preparation process, increased production and efficiency are achieved. This results in reduced production costs and also permits the system to operate over any time period of a given day with only limited operator intervention for manual inspection to ensure proper operation is being achieved. Such a system finds particular utility in settings, such as large hospitals, where a large number of doses of medications have to be prepared daily. Traditionally, these doses have been prepared manually in what is an exacting but tedious responsibility for a highly skilled staff. In order to be valuable, automated systems must maintain the exacting standards set by medical regulatory bodies, while at the same time simplifying the overall process and reducing the time necessary for preparing the medications.

Because syringes are often used as the carrier means for transporting and delivering the medication to the patient, it is advantageous for these automated systems to be tailored to accept syringes. However, the previous methods of dispersing the medication from the vial and into the syringe were very time consuming and labor intensive. More specifically, medications and the like are typically stored in a sealed vial. A conventional vial is formed of a body (i.e., glass) and is sealed with a membrane across the open end of the body. The membrane can be formed of any type of material that is typically used in this setting for sealing a container (e.g., vial) yet at the same time permit a user to puncture or pierce the membrane with an instrument to gain access to the inside of the container. In one exemplary embodiment, the membrane is formed of a rubber material that can be easily stretched across the open end while still providing the necessary seal.

A safety cap is securely attached to the vial to cover the exposed membrane and further seal the open end of the vial body. The safety cap is typically formed of a light, disposable material, such as a plastic, and is attached at the end in a tamper proof manner. For example, the safety cap is attached so that once it is removed, it can not be re-attached to the vial body. Thus, a vial that does not contain a safety cap is easily recognizable and indicates that either (1) the safety cap has previously been removed and medication in the vial has been withdrawn, (2) the safety cap was not properly attached and has accidently become displaced, (3) the vial has been tampered with, etc. In any event and unless the exact history of the particular vial is know, any vial that is missing a safety cap is ordinarily discarded and not used.

It will be understood that the parts of the vial are merely exemplary in nature and the many different tamper proof vial constructions are available. The common elements are that the vials each contain a membrane and the safety cap is easily removable but at the same time provides further protection of the membrane and also serves as an indicator of whether the vial has been used.

In conventional medication preparation, a trained person retrieves the correct vial from a storage cabinet or the like, confirms the contents and then removes the safety cap manually. This is typically done by simply popping the safety cap off with ones hands. Once the safety cap is removed, the trained person inspects the integrity of the membrane and cleans the membrane. An instrument, e.g., a cannula, is then used to pierce the membrane and withdraw the medication contained in the vial. The withdrawn medication is then placed into a syringe to permit subsequent administration of the medication from the syringe. Often, the membrane is first pierced with an instrument for injecting a diluent into the medication prior to withdrawal of the medication. This is a very time and labor intensive task. Thus, what is needed in the art and has heretofore not been available is a system and method for automating the medication preparation process and more specifically, an automated system and method for cleaning a cannula so that it can be reused numerous times to prepare different medications in different vials and then to transfer those medications to syringes so the medication can be administered to a patient.

SUMMARY OF THE INVENTION:

In accordance with an exemplary embodiment of the present invention this and other needs are achieved with a computer-implemented method and system for cleaning a contaminated cannula so that it may be reused. The method and system include moving the contaminated cannula from a drug reconstitution station where the cannula is used to prepare a drug solution into a first rinsing station where the cannula is cleaned. A database is referred to determine what drug solution the cannula has been contaminated with, and to determine a first amount of cleaning fluid that needs to be passed internally through the cannula, and a second amount of cleaning fluid that needs to be passed externally about the cannula so that there is effectively no contaminant remaining on the inside surface and the outside surface of the cannula. The first amount of cleaning fluid is passed internally through the cannula. The second amount of cleaning fluid is passed externally about the cannula. After the cannula is cleaned, the cannula is moved to the drug reconstitution station to prepare another drug solution.

DETAILED DESCRIPTION OF THE DRAWINGS:

Referring now to FIGS. 1–7, a preferred embodiment of the system 10 for cleaning and re-using a cannula in accordance with the present invention is illustrated. System 10 includes a rinsing station 12 for cleaning contaminated cannulas and a drug reconstitution station 14, which uses a clean cannula to prepare a medication or drug solution 16 within a vial 18 and subsequently transfers that medication to a syringe.

New technologies are being developed that provide automated systems for preparing and delivering medications. These technologies are being developed by the assignee of the present invention, and include the following non-provisional utility patent applications, all of which are hereby fully incorporated by reference in their entirety; entitled "SYRINGE BANDOLIER WITH CONTROL FEATURE", by inventor, Joel Osborne, filed on Nov. 15, 2001, U.S. Ser. No. 10/001,244; and entitled "SERIAL DATA TRAP AND DATA PROCESSING METHOD", by inventor, Dennis Tribble, filed on Nov. 21, 2001, U.S. Ser. No. 09/991,048.

These automated systems will include a number of stations, with one or more specific tasks being performed at each station. For example, at the drug reconstitution station 14, a syringe 62 is filled with a predetermined type of medication, at a predetermined volume and at a predetermined concentration all based upon information that has been stored or input into a software control unit 20 for the drug reconstitution station 14. For example, at the beginning of each day, a user may input into control unit 20 information regarding the medications to be prepared for that day. Preferably, to reduce the amount of times that the cannula needs to be cleaned, identical drug solutions (i.e., of the same concentration) are preferably mixed together at one time. However, if the operator desires, the drugs could be organized so that each patient's medications for the day are processed together and that each floor of patients in consecutive room numbers could be processed in that order to facilitate the organization of the medications downstream. Thus, based upon information stored in the control unit, information regarding what drug solution is to be prepared in each vial 18 as it is indexed through the automated apparatus is known and is traceable.

Figure 1:
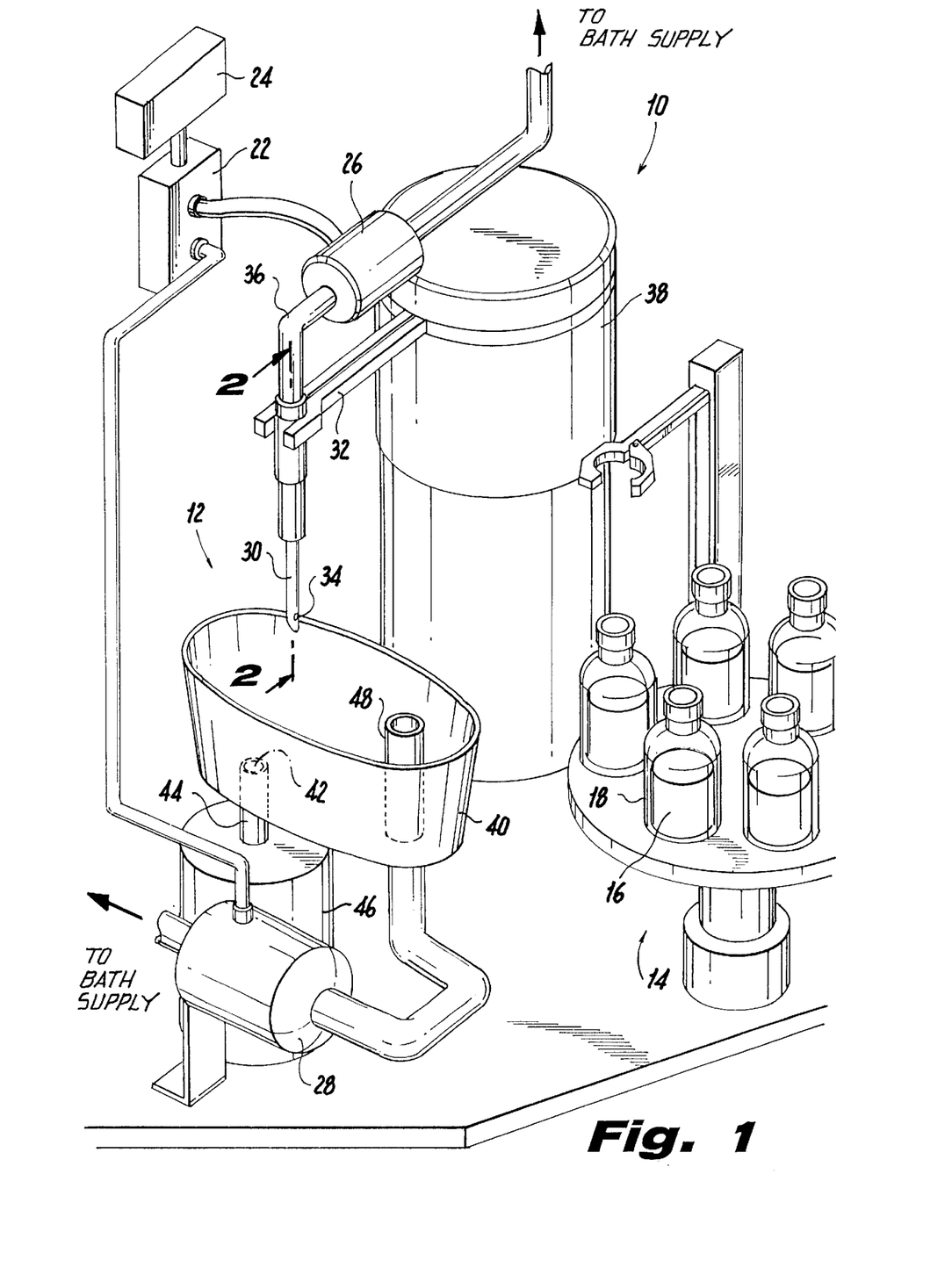
FIG. 1 is a perspective view of the system for cleaning and re-using a cannula in accordance with the present invention;.
Figure 2:
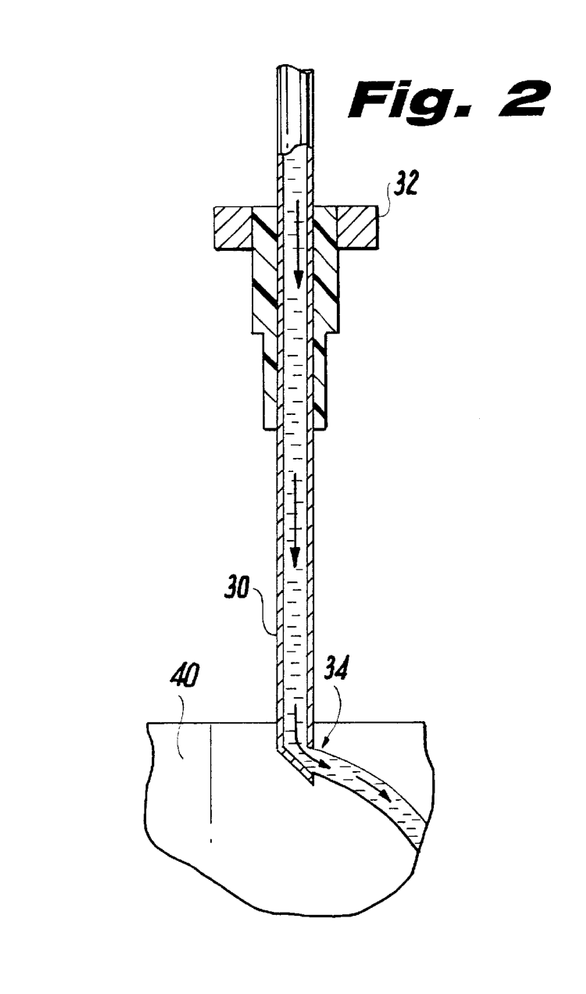
FIG. 2 is a cross-sectional view taken along the line 2—2 of FIG. 1 and looking in the direction of the arrows.
Figure 4:
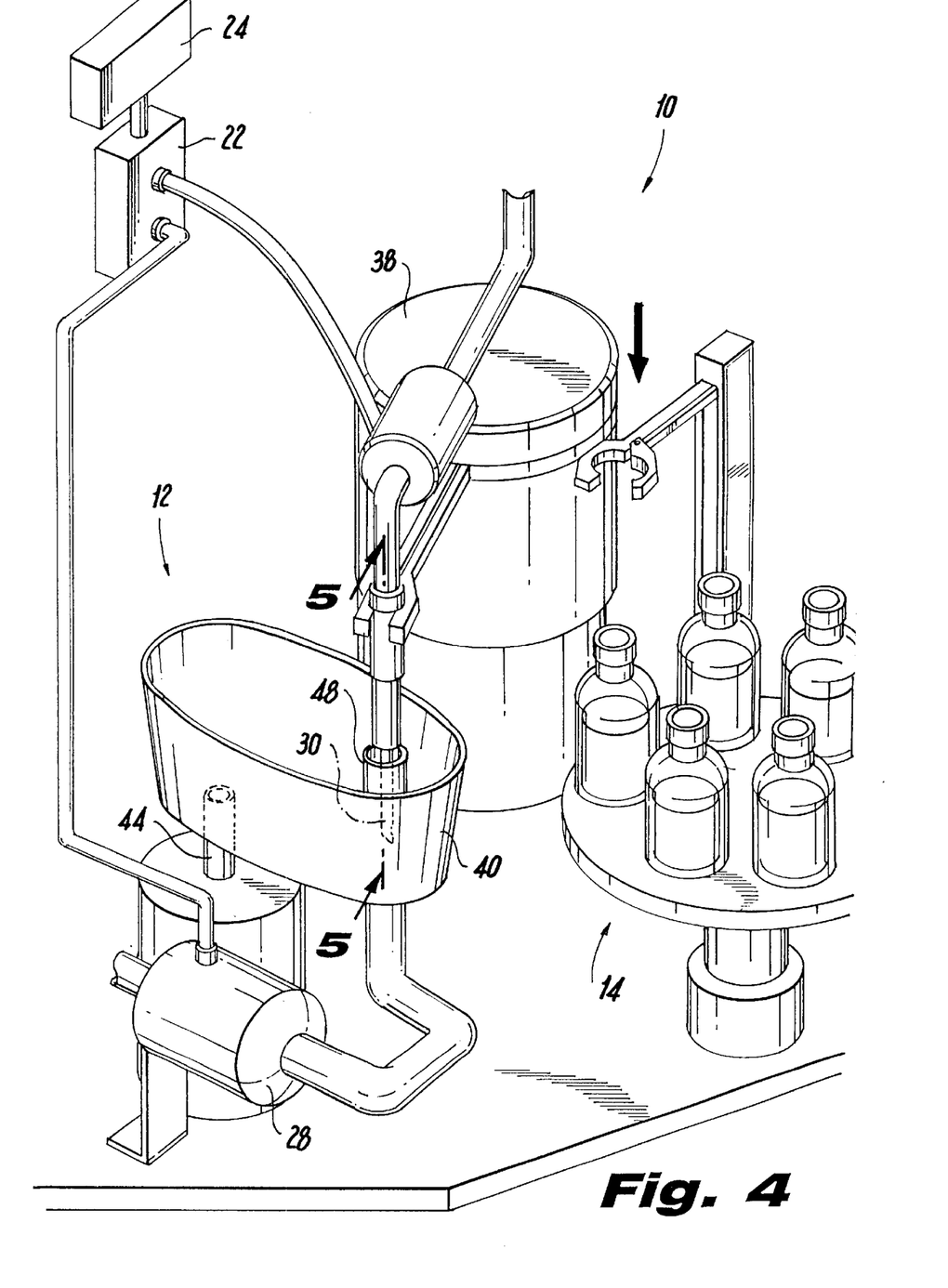
FIG. 4 is a perspective view of the system for cleaning the cannula of FIG. 1, with the cannula being indexed within the fount.
Figure 5:
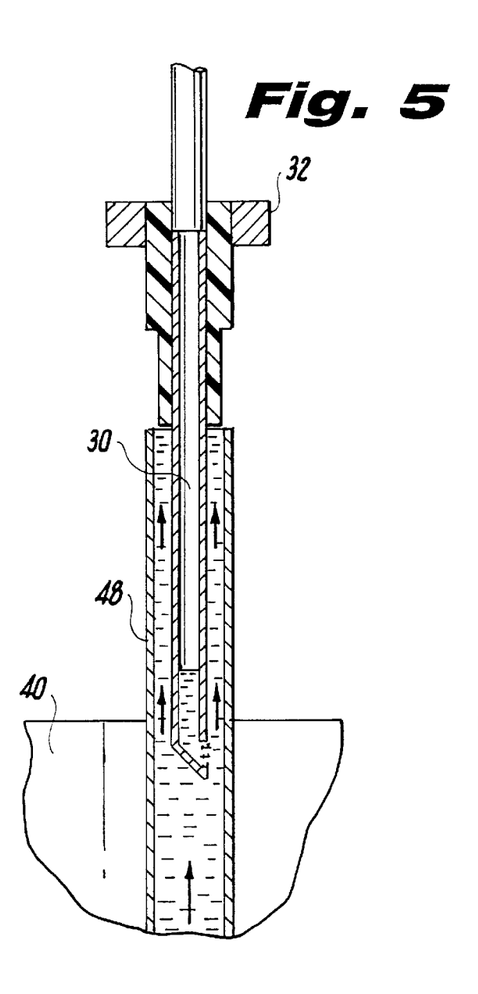
FIG. 5 is a cross-sectional view taken along line 5—5 of FIG. 4 and looking in the direction of the arrows.

Rinsing station 12 includes a control unit 22 that receives information from control unit 20 regarding what drug solution the cannula has been contaminated with. Based upon this information, control unit 22 will reference a database, preferably a look-up table 24, to determine how much cleaning fluid needs to be passed internally through the cannula and externally about the cannula so that there is effectively no contaminant remaining inside or outside of the cannula. Based upon this information, control unit 22 relays a signal to the pumps to control the activation of a first pump 26 and a second pump 28 to deliver the prescribed amount of cleaning fluid through cannula 30, as shown in FIGS. 1 and 2, and exteriorly about cannula 30, as shown in FIGS. 4 and 5.

Once the cannula 30 has been cleaned it can then be resent to the drug reconstitution station 14 to prepare a different drug solution in another vial and syringe. After cannula 30 is contaminated again and control unit 20 determines that the next drug solution to be prepared is different than the immediate previous one, the cannula is once again moved back to the cannula rinsing station 12 and the entire cleaning cycle is repeated. The drawings illustrate only one cannula being cleaned. However, one skilled in the art will readily recognize that a plurality of cannulas.

During the cleaning cycle, control unit 22 can be updated to associate the particular drug solution with the cannula that has just been cleaned. In addition, the control unit can also increment a count of the number of uses of the cannula, should it ever be determined that the cannula should be disposed of after a certain number of uses. Look-up table 24 contains information regarding how much cleaning fluid needs to be passed through and about the cannula to effectively clean it. The cleaning fluid is preferably sterile water, but the cleaning fluid could also be 0.9% sodium chloride or 5% dextrose or any other fluid that will effectively clean the cannula of the contaminant. The amount of cleaning fluid will vary from drug solution to drug solution, depending upon, inter alia, the drug solution information, including its concentration. The look-up table will contain an entry regarding how much cleaning fluid is required internally and externally for every drug solution that is to be prepared by the apparatus.

The cannula rinsing station 12 includes a cannula holder 32 and an indexing device 38 that moves the cannula 30 within the cannula rinsing station 12 and between the cannula rinsing station 12 and the drug reconstitution station 14. Cannula 30 is preferably a conventional needle that is commercially available and sold under the trade name TWO-FER™, which is available from the Baxa Company of Englewood, Colo. The needle is preferably a 19 gauge needle but could be of slightly larger or smaller size. This type of needle is preferred because as it penetrates through a conventional injectable vial 18, it does not core the rubber gasket in the vial. Thus, no foreign material is introduced into the vial. In addition, these types of needles have their outlet 34 in the sidewall as illustrated. As illustrated in FIG. 1, cannula 30 is fluidly connected to tubing 36, which is connected to a pump 26. Pump 26 is connected to a bath supply (i.e., a source of sterilizing fluid). As discussed above, once the proper amounts of sterilizing fluid that is required to be passed internally through the cannula is determined, the control unit 22 delivers a signal to pump 26 thereby controlling the actuation of pump 26 to deliver at least that amount of fluid to and through cannula 30, and out of the cannula via outlet 34 (see FIG. 2). The dispensed cleaning fluid is collected in a bath 40. Bath 40 has a drain outlet 42, which collects the cleaning fluid and any contaminant that it picks up, and dispenses that fluid via outlet 42 through a drain 44 to a collector 46 for disposal. FIG. 1 shows cannula 30 being offset with respect to a fount 48, which is used to clean the exterior surface of cannula 30. Thus, when the cleaning fluid exits from outlet 34, essentially none of the contaminant containing cleaning fluid is received within the fount.

Figure 3:
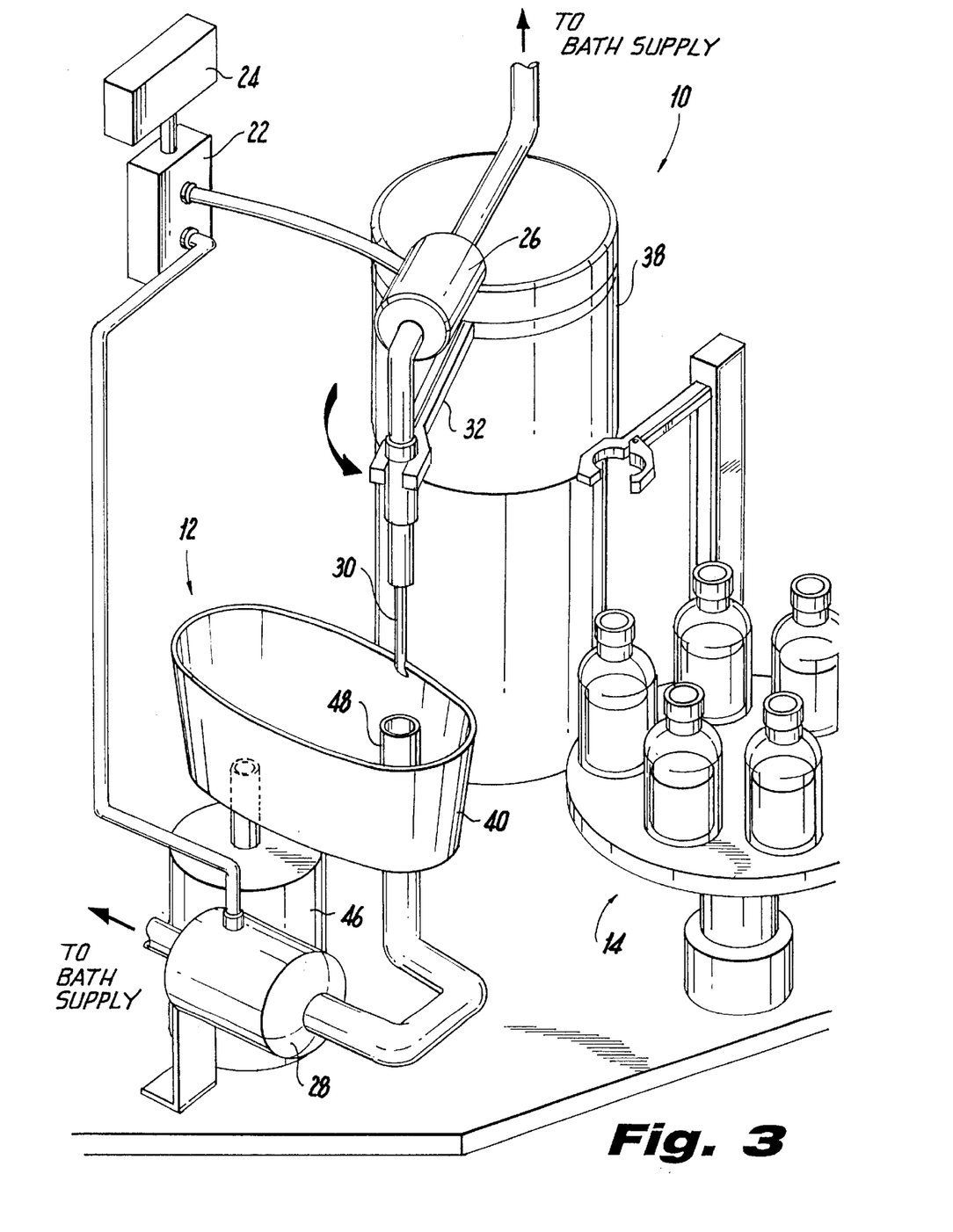
FIG. 3 is a perspective view of the system for cleaning the cannula of FIG. 1, with the cannula being indexed above a fount.

Once the determined amount of cleaning fluid has been passed internally through the cannula, the indexing device 38 is actuated to move the cannula 30 above fount 48 disposed within bath 40 (See FIG. 3). Indexer 38 then moves cannula 30 down into fount 48, as illustrated in FIGS. 4 and 5. Once the cannula 30 has been placed at a proper position within fount 48, control unit 22 once again delivers a signal to pump 28 to control the actuation of pump 28 to deliver the determined amount of cleaning fluid that needs to be passed externally about the cannula so that there is effectively no contaminant remaining outside of the cannula. Based on tests for various drug solutions, the following are examples of the amount of cleaning fluid which may be required for different drugs:

Gentamicin—a relatively low concentration drug product with a low allergy profile. The cleansing requirements will, therefore, be small, e.g., 10 mL internal and 5 mL external;

Ampicillin—a relatively higher concentration drug product with a high allergy profile. The cleansing requirements will, therefore, be relatively large, e.g., 30–40 mL internal and 20 mL external.

Intermediate drugs, such as, for example Cephalosporin antibiotics (e.g., Cefazolin, Cephalothin, Cephapirin, Ceftiroxime) will have internal cleaning volumes of 15–20 mL and external cleaning volumes of 10–15 mL.

As illustrated in FIG. 5, as the cleaning fluid is pumped up and around cannula 30, some cleaning fluid will be received within cannula 30. Thus, in some instances it may be desirable to move cannula 30 back to the position of FIGS. 1 and 2 to provide another rinse of the inside of cannula 30. Thus, a predetermined amount of cleaning fluid can once again be delivered through cannula 30 to ensure that no contaminant has been pushed back up into cannula 30. In this regard, for example, 5 ml of cleaning fluid can be pumped down through cannula 30. In fact, as little as 1 ml of cleaning fluid could be directed through the cannula for this third flush. Further, if desired, the cleaning procedure for cannula 30 can be reversed. More specifically, the exterior of the cannula could be cleaned first, then the interior. Further yet, if desired, a third flush could be delivered to the exterior of the cannula, as described above. Additionally, both the internal surface and external surface of the cannula can be cleaned simultaneously. In accordance with this cleaning procedure, the cannula is moved to the position shown in FIG. 3. Once the amounts of cleaning fluid is determined, control unit 22 can direct a signal to pumps 26 and 28 to thereby cause the desired amount of cleaning fluid to flow effectively simultaneously internally through and externally about the cannula.

Throughout the present specification, when referring to the amount of cleaning fluid that is to pass through the cannula or externally about the cannula, one skilled in the art would readily understand that the control unit 22 could be set to control the amount of time that the pumps 26, 28 are actuated. Most pumps operate at a constant flow rate and, therefore, setting the time is in effect equivalent to setting the amount or volume of cleaning fluid that is to be passed through or about cannula 30.

Figure 7:
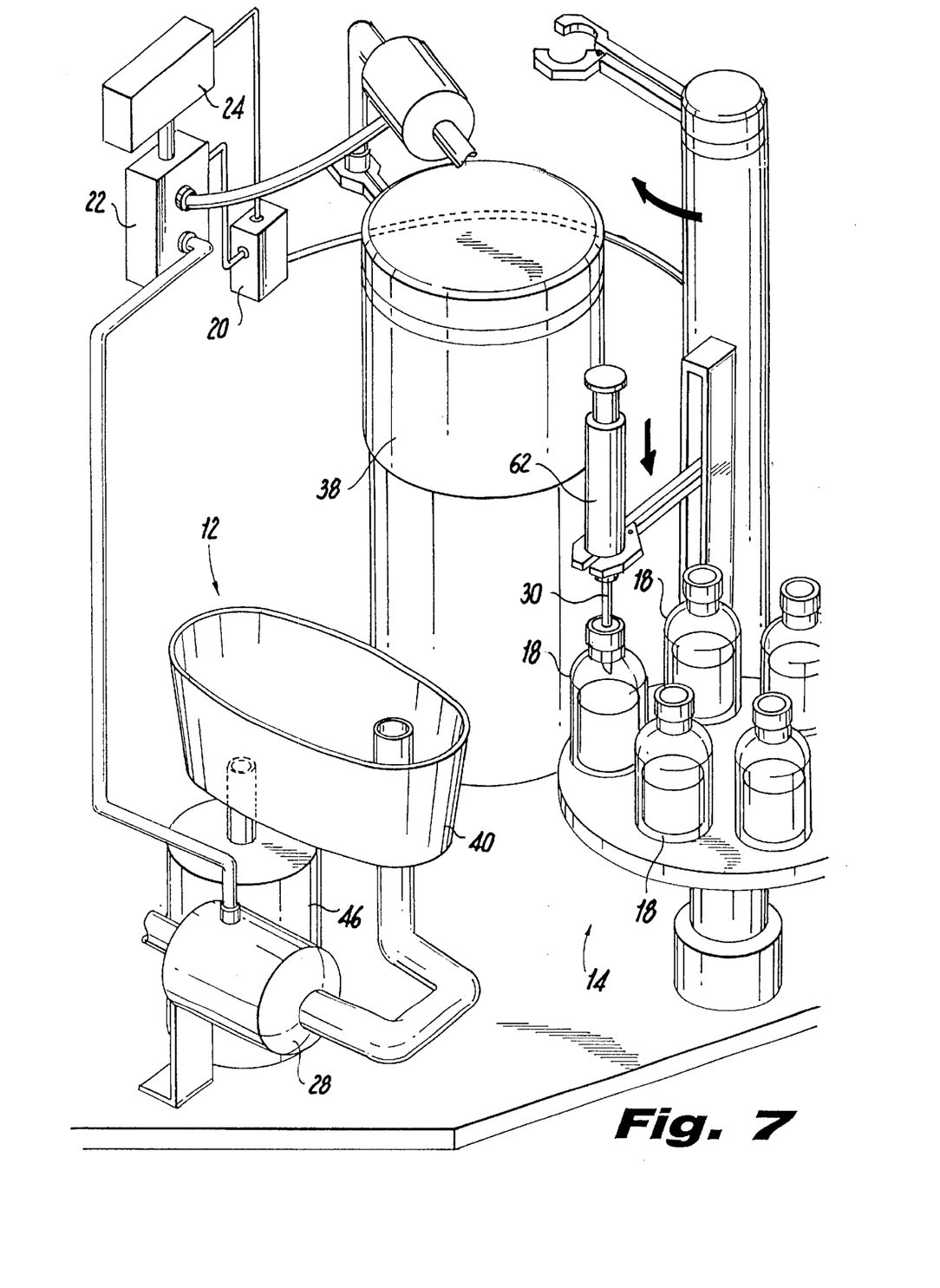
FIG. 7 is a perspective view of the system for cleaning the cannula, with the cannula at the drug reconstitution station.
Figure 8:
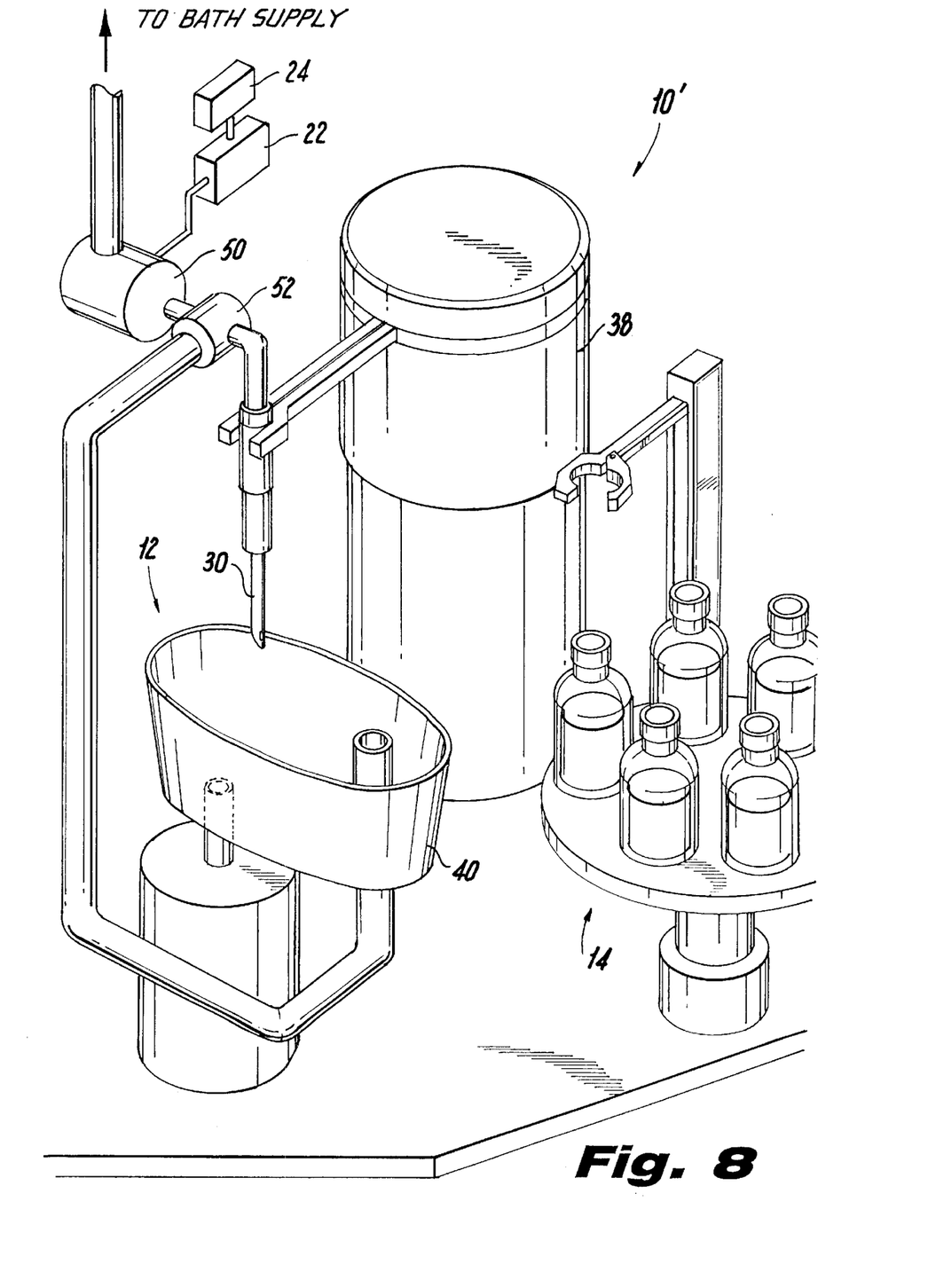
FIG. 8 is a perspective view of another embodiment of the system for cleaning and re-using a cannula in accordance with the present invention.

Referring now to FIG. 8, another embodiment of the present invention is illustrated. More specifically, this embodiment shows the use of a single pump 50 and a switching valve 52 to alternatively direct the cleaning fluid to the inside of cannula 30 or to the fount 48 so that the outside of cannula 30 can be cleaned. Otherwise, the rinsing and drug reconstitution stations illustrated in FIG. 8 are identical to those illustrated in FIGS. 1–7.

Figure 6:
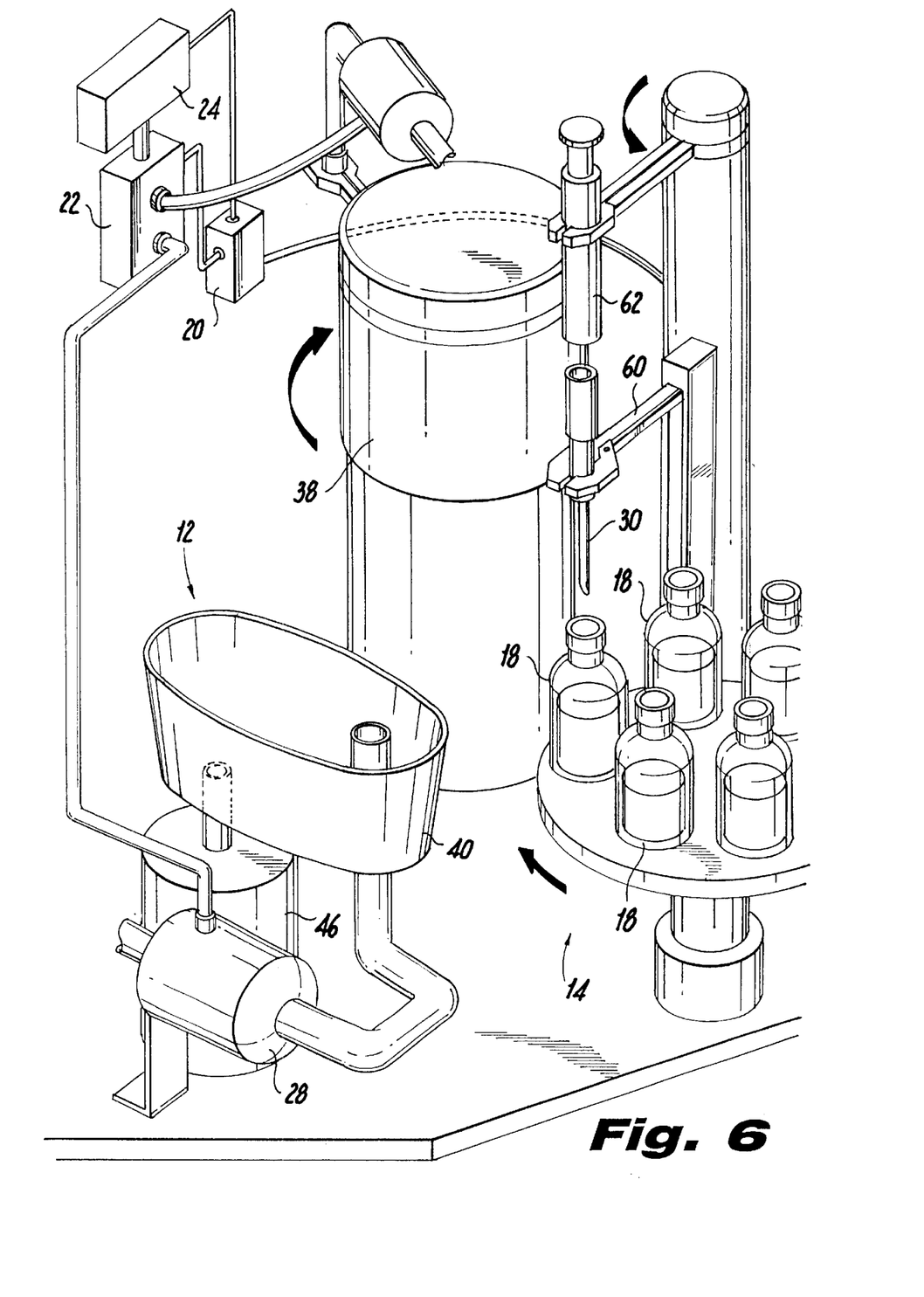
FIG. 6 is a perspective view of the system for cleaning the cannula, with the cannula at the drug reconstitution station.

Referring now to FIGS. 6 and 7, cannula 30 is shown transferred to a cannula holding device 60 within the drug reconstitution station 14. In the drug reconstitution station, cannula 30 is selectively connected to a syringe 62. At the appropriate time, cannula 30 is inserted into an insertable vial 18 through its membrane. Cannula 30 is used to inject a diluent into the vial so that a particular drug solution can be prepared within the vial. Once prepared, that drug solution is transferred back to syringe 62. The cannula can now be separated from the syringe. Syringe 62 can then be processed so that the medication is administered to a patient. Cannula 30 has now been contaminated, and can no longer be used without being cleaned first, unless it is for the same drug solution in the same concentration. Therefore, the cannula is transferred back to the rinsing station 12 so that it can be cleaned by the above procedure once again.

Figure 9:
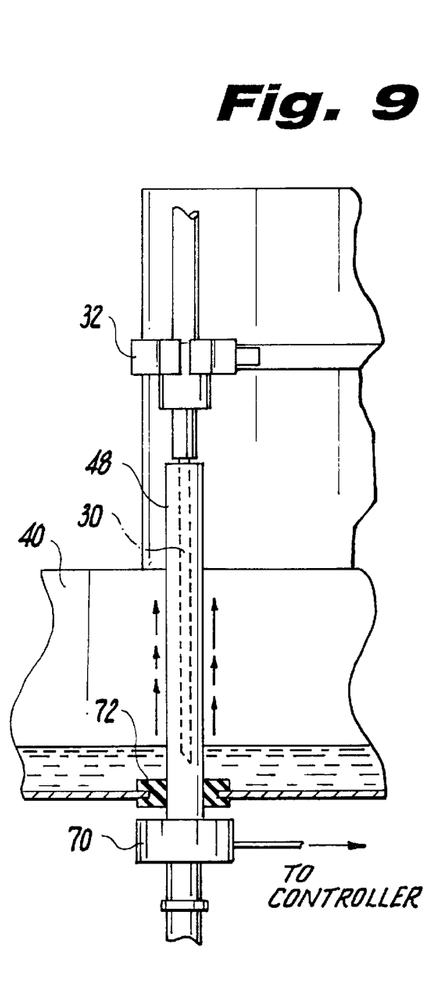
FIG. 9 is a partial sectional view of the cleaning station incorporating an ultrasonic cleaner.

Referring now to FIG. 9, fount 48 is illustrated with an ultrasonic transducer 70 mounted thereabout. With fount 48 receiving cannula 30, and fount 48 being filled with sterilizing fluid, ultrasonic transducer 70 can be actuated to ultrasonically clean the exterior surface of cannula 30. Depending upon the relative size of cannula 30 and fount 48, and the sterilizing fluid used, one skilled in the art would readily know how much power and for what duration to set the ultrasonic transducer 70 at to achieve effective cleaning of the cannula so that there is no contaminant remaining on the exterior surface of the cannula. The opening in bath 40 to receive fount 48 must be sealed with a sufficiently flexible gasket 72 to accommodate the actuation that will be imparted to fount 48 from ultrasonic transducer 70. In addition, if desired, ultrasonic transducer 70 could be mounted within bath 40.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. A computer-implemented method for cleaning a contaminated reusable cannula, comprising the steps of:

moving a particular cannula into a first rinsing station;

referencing a database to determine what drug solution the cannula has been contaminated with;

referencing the database to determine a first amount of cleaning fluid that needs to be passed internally through the cannula so that there is effectively no contaminant remaining inside of the cannula;

referencing the database to determine a second amount of cleaning fluid that needs to be passed externally about the cannula so that there is effectively no contaminant remaining outside of the cannula;

passing at least the first amount of cleaning fluid internally through the cannula; and passing at least the second amount of cleaning fluid externally about the cannula.

2. The method according to claim 1, further comprising the step of:
  updating the database to associate use of the drug solution with the cannula.

3. The method according to claim 1, further comprising the step of:
  updating the database to increment a count of a number of uses of the cannula.

4. The method according to claim 1, wherein the drug solution has a concentration, and wherein the first and second amounts of cleaning fluid are based on the concentration.

5. The method according to claim 1, wherein the determining steps each comprise a look-up into an electronic table of data.

6. The method according to claim 1, wherein the amount of fluid determined in said determining steps vary depending upon the drug solution that the cannula has been contaminated with.

7. The method according to claim 1, further comprising the step of:
  moving the cleaned cannula into a second drug reconstitution station.

8. The method according to claim 7, further comprising the step of:
  contaminating the cannula with a second drug solution by injecting the cannula into an injectable vial to reconstitute the second drug solution at a second station.

9. The method according to claim 8, further comprising the steps of:
  referencing the database to determine a third amount of cleaning fluid that needs to be passed internally through the cannula so that there is effectively no contaminant remaining inside the cannula;
  referencing the database to determine a fourth amount of cleaning fluid that needs to be passed externally about the cannula so that there is effectively no contaminant remaining outside the cannula;
  passing at least the third amount of cleaning fluid internally through the cannula; and
  passing at least the fourth amount of cleaning fluid externally about the cannula.

10. The method according to claim 1, wherein passing the first amount of cleaning fluid step occurs before the passing the second amount of cleaning fluid step occurs.

11. The method according to claim 10, further comprising the step of:
  passing a third predetermined amount of cleaning fluid internally through the cannula after passing the second amount of cleaning fluid steps occurs.

12. The method according to claim 11, wherein the third predetermined amount of cleaning fluid is approximately 5 ml.

13. The method according to claims 11, wherein the third predetermined amount of cleaning fluid is approximately 1 ml.

14. The method according to claim 1, wherein passing the second amount of cleaning fluid step occurs before the passing the first amount of cleaning fluid step occurs.

15. The method according to claim 14, further comprising the step of:
  passing a third predetermined amount of cleaning fluid externally about the cannula after the passing the first amount of cleaning fluid step occurs.

16. The method according to claim 15, wherein the third predetermined amount of cleaning fluid is approximately 5 ml.

17. The method according to claim 16, wherein the third predetermined amount of cleaning fluid is approximately 1 ml.

18. The method according to claim 1, wherein passing the first amount of cleaning fluid step occurs substantially simultaneously with the passing the second amount of cleaning fluid step.

19. The method according to claim 1, wherein the cleaning fluid is sterile water.

20. The method according to claim 1, wherein the cleaning fluid is 0.9% sodium chloride.

21. The method according to claim 1, wherein the cleaning fluid is 5% Dextrose.

22. The method according to claim 1, wherein, before passing at least the second amount of cleaning fluid step, further comprising the step of:
  moving the cannula into a second position within the first rinsing station so that the cannula is essentially disposed within a fount, wherein the second amount of cleaning fluid is passed from a source through the fount and externally about the cannula.

23. A system for cleaning a reusable cannula comprising:
  a drug reconstitution station operative to prepare a first drug solution by use of a cannula thereby contaminating the cannula;
  a cannula rinsing station operative to clean the cannula internally and externally with a cleaning fluid so that there is effectively no contaminant remaining inside and outside of the cannula;
  the cannula being movable between the drug reconstitution station and the cannula rinsing station;
  whereby after the cannula has been cleaned at the cannula rinsing station, the cannula can be reused in the drug reconstitution station to reconstitute a second drug solution that is different than the first drug solution.

24. The system of claim 23, further comprising a database populated with a predetermined minimum amount of cleaning fluid data required to clean a plurality of drug solutions; and wherein the cannula rinsing station references the database to determine a minimum amount of cleaning fluid for a particular drug solution.

25. The system of claim 24, wherein the amount of cleaning fluid is governed by the particular drug solution introduced into the cannula by the drug reconstitution station.

26. The system of claim 24, wherein the database includes an electronic look-up table.

27. The system of claim 23, wherein the amount of cleaning fluid is governed by a particular drug solution introduced into the cannula by the drug reconstitution station.

28. A computer-implemented method for cleaning a contaminated cannula so that it may be reused, comprising the steps of:
  moving a particular cannula into a first rinsing station;
  referencing a database to determine what drug solution the cannula has been contaminated with;
  referencing the database to determine a first amount of cleaning fluid that needs to be passed internally through the cannula so that there is effectively no contaminant remaining inside of the cannula;
  referencing the database to determine a power and time setting for an ultrasonic transducer that is placed externally about a fount which receives the cannula;
  passing at least the first amount of cleaning fluid internally through the cannula; and
  activating the ultrasonic transducer at the determined power and time setting so that there is effectively no contaminant externally about the cannula.

* * * * *